United States Patent [19]

Portnoy

[11] Patent Number: 4,759,761
[45] Date of Patent: Jul. 26, 1988

[54] CATADIOPTRIC INTRAOCULAR LENS

[75] Inventor: Vladimir Portnoy, Irvine, Calif.

[73] Assignee: Allergan, Inc., Irvine, Calif.

[21] Appl. No.: 926,867

[22] Filed: Nov. 3, 1986

Related U.S. Application Data

[63] Continuation of Ser. No. 839,430, Mar. 13, 1986, abandoned.

[51] Int. Cl.⁴ .............................................. A61F 2/16
[52] U.S. Cl. .......................................................... 623/6
[58] Field of Search ........................................... 623/4–6

[56] References Cited

U.S. PATENT DOCUMENTS

| | | | |
|---|---|---|---|
| 3,515,461 | 6/1970 | Casas et al. | 350/199 |
| 3,529,888 | 9/1970 | Buchroeder | 350/184 |
| 3,711,185 | 1/1973 | McKinley | 350/201 |
| 3,926,505 | 12/1975 | Rayces | 350/201 |
| 4,061,420 | 12/1977 | Kaprelian et al. | 350/199 |
| 4,074,368 | 2/1978 | Levy, Jr. et al. | 623/6 |
| 4,342,503 | 8/1982 | Shafer | 350/443 |
| 4,482,219 | 11/1984 | Canzek | 350/444 |
| 4,487,483 | 12/1984 | Versteeg | 350/444 |
| 4,581,031 | 4/1986 | Koziol et al. | 623/6 |

FOREIGN PATENT DOCUMENTS

| | | | |
|---|---|---|---|
| 1103399 | 5/1955 | France | 623/6 |
| WO83/01566 | 5/1983 | PCT Int'l Appl. | 623/6 |
| 2119960 | 1/1986 | United Kingdom | 623/6 |

OTHER PUBLICATIONS

"Galilean Telescope Using the Anterior Chamber Implant as Eye-Piece: a Low-Visual-Acuity Aid for Macular Lesions", (chapter 21), Book–Initra-Ocular Lenses and Implants, by Peter Choyce, 1964, pp. 156–161.

Primary Examiner—Ronald L. Frinks
Attorney, Agent, or Firm—Gordon L. Peterson

[57] ABSTRACT

Substantial magnification while preserving a wide field of view is obtained in the treatment of macular degeneration by implanting within the eye a lens having interior mirrored surfaces forming a folded telescope of either the Gregorian type or the Cassegrain type.

20 Claims, 2 Drawing Sheets

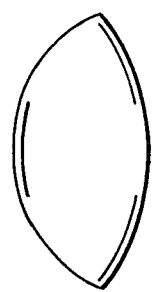   
FIG 2a  FIG 2b  FIG 2c  FIG 2d
  
FIG 2e  FIG 2f  FIG 2g

CATADIOPTRIC INTRAOCULAR LENS

This application is a continuation of application Ser. No. 839,430 filed Mar. 13, 1986, entitled Catadioptric Intraocular Lens now abandoned.

This invention relates to intraocular lenses, and more particularly to a catadioptric lens for implantation in the eye for visual rehabilitation of macular degeneration.

BACKGROUND OF THE INVENTION

The retina disease known as macular degeneration causes an absence of central vision in the patient's eye due to a deficiency of the central retinal portion. In order to restore a certain amount of useful vision to the patient, it is necessary to greatly magnify the object at which the patient looks. This can be accomplished to some degree by eyeglasses, magnifiers or telescopes; however, several problems exist.

Spectacle glasses must have quite high power for sufficient magnification (up to +20D). Problems with spectacle magnifiers are (1) short working distance (only 8.3 cm for 3× magnification; and (2) weight and fitting the separation between the spectacle and the eye must be exact. Magnifiers have a very restricted visual field (a 3× magnifier of 5 cm diameter has about a 3 cm viewing field). They also have a short working distance and are inconvenient to use. Telescopes are used for distant object viewing and consequently have a long working distance. They must be light-weight and have a very restrictive visual field (less than 20 degrees at 2× magnification, and down to 4 degrees at high magnification, as compared to a minimum field angle of 30° required for comfortable vision). Koester, C. J., and Donn, A., International Pat. No. WO83/01566, disclose a telescope system as continuation of high power glasses (up to 30D) and high negative intraocular lens (down to −100D). This combination theoretically might give higher viewing field up to 30 degrees for 2.5× which is limited by spectacle glasses, as similar to spectacle magnifier. This arrangement is inconvenient to high power spectacles and even more restrictive in fitting (for +30 D spectacle variation in distance from the spectacle to the eye must be kept within 1 mm).

SUMMARY OF THE INVENTION

The present invention overcomes the above-noted deficiencies by providing an increased visual field while eliminating the fitting problem and providing improved flexibility in magnification variations. It achieves distance magnification without severe field restrictions by providing a single intraocular lens with built-in mirrored surfaces which produce the effect of a folded telescope with a long focal distance. The intraocular position of the catadioptric lens is very close to the natural lens position, and consequently permits a maximum visual field with any optical aid and given magnification.

The preferred embodiment of the invention contemplates the use of a 3× power lens which permits a visual field about one-third the size of the unmagnified field, and a field angle of at least 40 degrees. This catadioptric lens solves the problem of short working distance in near vision (reading magnification) which exists in spectacle magnifiers and hand-held magnifiers. It also offers much larger visual field.

The catadioptric lens of this invention offers flexibility in magnification change without sacrificing quality. Additional magnification can be achieved by using spectacle glasses with a total magnification similar to a microscope (8× power) while retaining a practical visual field and working distance. The actual configuration of the lens can vary depending upon the particular configuration of the eye, the amount of magnification required, and whether or not the patient also wears glasses.

It is therefore the object of the invention to produce magnification with a maximum field of vision and enlarged near-vision working distance by means of a catadioptric intraocular lens forming a two-mirror folded telescopic system by using one or more solid intraocular elements. In the examples below, only single-element systems will be described.

BRIEF DESCRIPTION OF THE DRAWINGS

FIGS. 2a through 2g are examples of alternative forms of single-element catadioptric intraocular lenses which can be used in connection with this invention.

DESCRIPTION OF THE PREFERRED EMBODIMENT

Figure 1A:
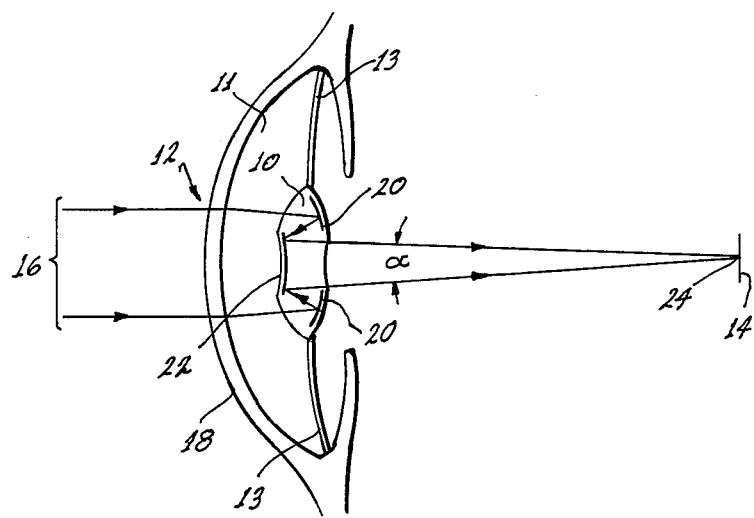
FIG. 1a is a schematic diagram illustrating the placement of the lens of this invention in the anterior chamber.

FIG. 1a shows an intraocular lens which includes a lens or an optic body 10 implanted within the anterior chamber 11 of an eye 12, as might be done for either a phakic or an aphakic patient. (The crystalline lens of a phakic patient has been omitted in FIG. 1a for clarity.) The lens 10 may be supported in the eye 12 by appropriate fixation means or haptics 13.

The light from the object 16 is refracted to some degree by the cornea 18 and is then reflected by an annular mirrored surface or generally anteriorly facing reflector 20 within the lens 10. The reflected light is then projected against a circular mirrored surface or generally posteriorly facing reflector 22 located centrally of the forward portion of the lens 10. The surface 22 reflects the light back toward the retina 14 where it is focused to form the magnified image. The two-mirror combination within the lens 10 provides an optic which produces a folded telescope effect in which the angle of incidence α is minimized so as to provide a maximum amount of magnification.

Because the folded telescope effect is created within the eye itself, the field of view produced by the lens of the invention is substantially larger than the field of view produced by external magnification and leaves room for supplemental external magnification for an overall power increase. The lens 10 may be constructed of any medical-grade plastic, such as PMMA, normally used in intraocular lens optics. The mirrored surfaces 20, 22 may consist of thin layers of platinum, silver, aluminum or other appropriate reflective materials embedded in the lens 10 by conventional methods during the process of fabrication.

Figure 1B:
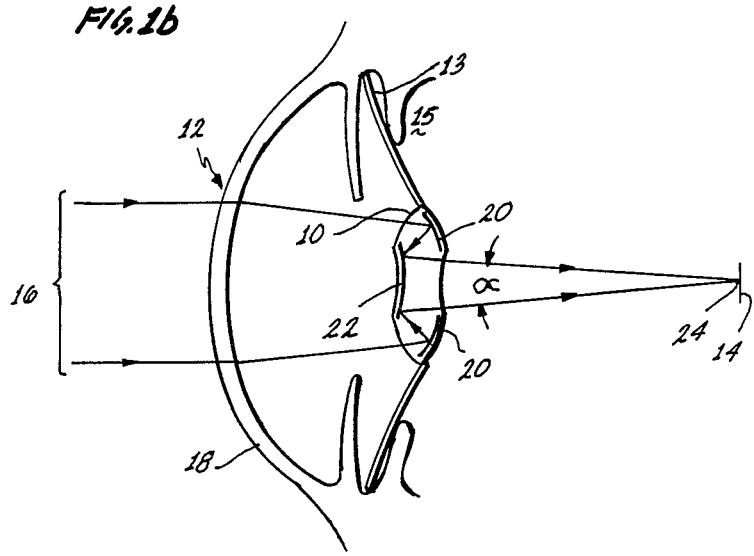
FIG. 1b is a schematic diagram illustrating the placement of the lens of this invention in the posterior chamber.

FIG. 1b shows the lens 10 implanted in the posterior chamber 15 of the eye 12, as could be done in an aphakic patient. FIGS. 2a through 2g show various other configurations of lenses incorporating a two-mirror folded telescope system which could be used in place of the preferred convexo-concave Cassegrain-type embodiment shown in FIGS. 1a and 1b. FIGS. 2a through 2d illustrate convexo-convex, concavo-convex, convexo-concave, and concavo-concave lens bodies respectively, with mirrored surfaces forming a folded telescope system of the Gregorian form. As shown in FIGS. 2a through 2d, the annular mirrored surfaces are concave and the circular mirrored surfaces are also concave. As shown in FIGS. 1a and 1b, the annular mirrored surface 20 is concave and the circular mirrored surface 22 is convex. The corresponding mirrors of FIGS. 2e through 2g are similarly shaped. FIGS. 2e through 2g illustrate convexo-convex, concavo-convex, and concavo-concave lens bodies, respectively, with mirrored surfaces forming a folded telescope system of the Cassegrain form.

I claim:

1. An intraocular lens for the rehabilitation of macular degeneration, comprising:
   (a) a transparent body having front and rear surfaces;
   (b) a substantially circular reflecting layer in said body adjacent said front surface;
   (c) an annular reflecting layer in said body adjacent said rear surface; and
   (d) means for retaining said lens inside the eye;
   (e) said reflective layers operating as a folded telescope when implanted within the eye.

2. The lens of claim 1, in which the curvature of said reflecting layers is substantially the same as the curvature of the adjacent surface.

3. The lens of claim 1, in which said folded telescope is of the Gregorian form, and said reflecting layers are concave.

4. The lens of claim 3, in which said body is convexo-convex.

5. The lens of claim 3, in which said body is concavo-convex.

6. The lens of claim 3, in which said body is convexo-concave.

7. The lens of claim 3, in which said body is concavo-concave.

8. The lens of claim 1, in which said folded telescope is of the Cassegrain form, and said annular and circular reflecting layers are concave and convex, respectively.

9. The lens of claim 8, in which said body is convexo-convex.

10. The lens of claim 8, in which said body is concavo-convex.

11. The lens of claim 8, in which said body is convexo-concave.

12. The lens of claim 8, in which said body is concavo-concave.

13. The lens of claim 1, in which said body is adapted to be retained within the anterior chamber of said eye.

14. The lens of claim 1, in which said body is adapted to be retained within the posterior chamber of said eye.

15. An intraocular lens for implantation in the eye comprising:
   an optic body having anterior and posterior surfaces;
   a generally anteriorly facing reflector carried by said optic body;
   a generally posteriorly facing reflector carried by said optic body, said reflectors being positioned in said optic body so that light from an object passing through the anterior surface and striking the anteriorly facing reflector is reflected from the anteriorly facing reflector to said posteriorly facing reflector and from said posteriorly facing reflector through said posterior face; and
   fixation means for fixing the optic body in the eye.

16. A lens as defined in claim 15 wherein the anteriorly facing reflector is concave.

17. A lens as defined in claim 15 wherein the anteriorly facing reflector is annular.

18. A lens as defined in claim 15 wherein said reflectors are within the optic body.

19. An intraocular lens for implantation in the eye comprising:
   an optic including a reflecting telescope;
   fixation means for fixing the optic in the eye; and
   said reflecting telescope having reflecting surfaces for reflecting light in the eye when the intraocular lens is implanted in the eye.

20. An intraocular lens for implantation in the eye comprising:
   an optic including an optic body and a plurality of reflective surfaces carried by the optic body to provide a single optical element serving as a telescope; and
   fixation means for fixing the optic in the eye.

* * * * *